US006258386B1

(12) United States Patent
Xia et al.

(10) Patent No.: US 6,258,386 B1
(45) Date of Patent: Jul. 10, 2001

(54) SMILAGENIN AND ITS USE

(75) Inventors: Zongqin Xia, Shanghai (CN); Ian Rubin, Castle Donington (GB); Brian Whittle, Hornsea (GB); Philip Gunning, Saffron Walden (GB); Yaer Hu, Shanghai (CN); Jonathan Brostoff, London; Weijun Wang, Huntingdon, both of (GB)

(73) Assignee: Phytopharm PLC, Cambridgeshire (GB)

( * ) Notice: Subject to any disclaimer, the term of this patent is extended or adjusted under 35 U.S.C. 154(b) by 0 days.

(21) Appl. No.: 09/362,328

(22) Filed: Jul. 28, 1999

(30) Foreign Application Priority Data

Mar. 8, 1999 (GB) .................................................. 9905275

(51) Int. Cl.$^{7}$ ..................................................... A61K 35/78
(52) U.S. Cl. ............................................................. 424/725
(58) Field of Search ................................. 424/195.1, 725

(56) References Cited

U.S. PATENT DOCUMENTS 5,804,239 * 9/1998 Wiersma .

FOREIGN PATENT DOCUMENTS 1124514 12/1994 (CN) .
4303214 2/1993 (DE) .
9916786 8/1999 (WO) .

OTHER PUBLICATIONS

"Sarsasapogenin: Mechanism in Treating Senile Dementia." by Ningyu, et al. (Paper 62). Proceedings of The 6th International Symp. of the International Isotope Society, Philadelphia, 1997.

Phytochemistry (1978), 17(11), 1923–1926 Document Entitled "Steroidal Sapogenins from Leaves of Agaveae Species," by Blunden, et al.

* cited by examiner

*Primary Examiner*—Francisco Prats
*Assistant Examiner*—Susan D. Coe
(74) *Attorney, Agent, or Firm*—Oppenheimer Wolff & Donnelly LLP

(57) ABSTRACT

The invention discloses the use of a smilagenin in the treatment of cognitive disfunction and similar conditions. Methods of treatment, and pharmaceutical compositions are also disclosed.

8 Claims, 2 Drawing Sheets

SMILAGENIN AND ITS USE

The present invention relates to smilagenin and its use in treating cognitive disfunction and allied conditions; and to compositions for use in such treatments. The invention is also concerned with the treatment of conditions that are characterised by a deficiency in the number or function of membrane-bound receptors. In the following, the present invention will be described principally with reference to the treatment of Alzheimer's disease (AD) and senile dementia of the Alzheimer's type (SDAT), where deficiencies in a number of receptor types have been demonstrated. However, it is to be understood that the present invention relates generally to the treatment of conditions attributable to intrinsic pathological conditions and/or exposure to adverse environment conditions these conditions being characterised by a deficiency in the number of function of membrane-bound receptors or a deficiency in transmission at the junctions between neurones or at the junctions of neurones and effector cells.

Conditions of the type mentioned above include Parkinson's disease, Lewi body dementia, postural hypotension, autism, chronic fatigue syndrome, Myasthenia Gravis, Lambert Eaton disease, diseases and problems associated with Gulf War Syndrome, occupational exposure to organophorphorus compounds and problems associated with ageing.

Alzheimer's disease (AD) and senile dementia of the Alzheimer's type (SDAT) are grave and growing problems in all societies where, because of an increase in life expectancy and control of adventitious disease, the demographic profile is increasingly extending towards a more aged population. Agents which can treat, or help in the management of, AD/SDAT are urgently required.

Age-associated memory impairment (AAMI) is a characteristic of older patients who, while being psychlogically and physically normal, complain of memory loss. It is a poorly defined syndrome, but agents which are effective in treatment of AD/SDAT may also be of value in these patients.

Research into AD/SDAT is being carried out by traditional and conventional medical research methods and disciplines. In conventional medicine, there are several approaches to the treatment of AD/SDAT. It is known that the biochemical processes subserving memory in the cerebral cortex are (at least in part) cholinergically-mediated. Those skilled in the art will know that "cholinergically mediated" mechanisms may be directly attributable to acetylcholine acting on receptors, and these are direct effects. Other, clinically useful effects may also be caused by modulation of release of acetylcholine from pre-synaptic nerve endings or inhibition of enzymes that destroy acetylcholine. These modulating factors may be exerted through neurones where the mediator is non-cholinergic; these are referred to as indirect effects. Some attempts at treatment have focussed on the role of other mediators such as 5-hydroxytryptamine, which is a mediator in other areas of brain, such as the mid-brain nuclei. However, since fibres from these areas are projected forward into the cerebral cortex where the primary transmitter is acetylcholine, attention has focussed on the management of this mediator in the search for appropriate therapeutic agents.

Cholinergic strategies for the treatment of AD/SDAT have been directed at several points along the pathway of formation, synaptic release and removal of released acetylcholine.

One approach involves treatment with high doses of lecithin and other precursors of acetylcholine. This is of limited use in producing sustained improvements in cognitive performance.

Another approach involves the use of vegetable drugs such as Polygalae root extract, which has been shown to enhance choline-acetylcholine transferase (CAT) activity and nerve growth factor (NGF) secretion in brain. Oral administration of NGF has no effect on central nervous system neurons because it is a high molecular weight protein that cannot pass through the blood-brain barrier. However, agents which can pass through the blood-brain barrier and have a stimulating effect on NGF synthesis in the central nervous system have been proposed for the improvement of memory-related behaviour.

The results of a third clinical approach, which uses cholinesterase inhibitors such as tacrine hydrochloride, have been marginally more positive than the above. Substances obtained from plants used in Chinese and Western medicine, for example huperzine, galanthamine, and physostigmine have all been shown to be of some—although limited—benefit in the treatment of AD/SDAT in clinical studies and also in laboratory models. All of these substances are inhibitors of acetylcholine esterase (AChE). In patients with AD/SDAT, there may be reduced synthesis of acetylcholine (ACh), reduced efficiency in release of ACh from presynaptic stores, and a decrease in the number or function of postsynaptic ($M_1$) receptors. Reductions in pre-synaptic $M_2$ receptors have also been shown. The beneficial effect of AChE inhibitors is attributed to enhancement of acetylcholine levels at synapses in brain by slowing down the destruction of released transmitter.

Compositions which modulate cholinergic function are known to affect memory and recall. For example, nicotine stimulates nicotinic acetylcholine receptors, and the short lived memory enhancing effects of cigarette smoking are thought to be due to the effect of nicotine. Scopolamine, an antagonist of acetylcholine, will produce amnesia and impaired cognitive function manifesting in psychomotor tests as a prolongation of simple reaction times, possibly as a result of impaired attention, and is used for this purpose as an adjunctive analgesic treatment. The amnesic effect of scopolamine can be antagonised by nicotine.

There are two families of nicrotinic receptor subtypes ($\alpha$ and $\beta$), and each includes four subgroups which differ in ligand specificity. The role of nicrotinic receptors in the CNS is not well understood at the molecular level. It is possible that agents binding to nicrotinic receptors may modify the rate of turnover at muscarinic receptor sites in brain. Nicotinic receptors are ligand-gated ion channels, and their activation causes a rapid (millisecond) increase in cellular permeability to $Na^+$ and $Ca^{++}$, depolarisation and excitation.

Another class of cholinergic receptors can be stimulated by muscarine. Such muscarinic (M) receptors are G protein-coupled receptors. Responses of muscarinic receptors are slower; they may be excitatory or inhibitory. They are not necessarily linked to changes in ion permeability. Five types of muscarinic receptors have been detected by cholinergic receptor cloning, and are designated as $m_1$–$m_5$. Pharmacological effects are associated with four of the cloned receptors and they are designated as $M_1$–$M_4$ based on pharmacological specificity.

Using specific receptor proteins and monoclonal antibodies, it has been possible to further localise muscarinic receptors in brain as $m_1$ (postsynaptic) and $m_2$ (presynaptic).

In heart, $M_2$ receptors are postsynaptic. Presynaptic muscarinic receptors are thought to be inhibitory, the binding of ACh to these receptors attenuating the release of further ACh to provide a negative feedback mechanism for Ach release. Selective $M_2$ receptor antagonists which are preferentially distributed to the brain may therefore be useful in treating Alzheimer's disease.

It is known that, in disease states such as AD/SDAT, there is general neuronal loss and deficits in cholinergic nerve function. It has been speculated that the high affinity nicotinic binding sites in the remaining cholinergic neurons might be converted to low affinity binding sites in treating such diseases, thereby sustaining transmitter release. By lowering the affinity of the nicotinic binding sites, a quick desensitising process is avoided.

Agonist activation at nicrotinic receptors in brain has rapid onset and offset. A decreased affinity of the nicotinic receptors will reduce the desensitisation process. Schwarz R. D. et al (J. Neuro Chem 42, (1984), 1495–8) have shown that nicotine binding sites are presynaptically located on cholinergic (and also 5-hydroxytryptaminergic and catecholaminergic) axon terminals. A change in high affinity binding sites on AD/SDAT may also induce a change in the modulatory effect the nicotinic binding sites may have on other transmitter systems.

Presynaptic cholinergic mechanisms are also under inhibitory control by GABAergic neurons and this inhibition is thought to be intensified in AD/SDAT. Removal or reduction of this inhibition intensifies presynaptic cortical cholinergic activity and enhances cognitive processing.

The interactions of interneuronal fibres innervated by nicotine (reducing binding affinity), and dis-inhibition of GABAergic fibres both have a presynaptic locus.

This is a simplistic model of central transmission, but provides a framework for understanding the attempts which have been made to increase the effective concentration of acetylcholine in central synapses. This further illustrates the concept of direct and indirect action. There are disadvantages attaching to the three conventional therapeutic approaches to AD/SDAT treatment mentioned above. ACh precursor supplementation, agonist replacement and acetylcholine esterase inhibition. These treatments may result in a short-term increase in the availability of ACh which may activate feedback mechanisms resulting in the desensitisation of postsynaptic receptors. On theoretical grounds, long term benefits would not be predicted and when treatment is interrupted, any benefits in management of AD/SDAT and AMMI disappear and the condition may even be aggravated.

It has been shown that a compound with $M_1$ agonist and $M_2/M_3$ antagonist activity improved cognitive performance in SDAT patients (Sramak et al, Life Sciences vol. 2, No. 3, 195–202, 1997). However, this compound causes unacceptable cholinergic side effects, such as fatigue, diarrhoea and nausea.

A more radical approach to AD/SDAT and AAMI aims to increase the number of postsynaptic ($M_1$) receptors, in brain. It is known from Chinese Patent No. CN1096031A, that sarsasapogenin (SaG) can up-regulate $M_1$ cholinergic receptors and also down-regulate (i.e. move towards normal levels of) β-adrenergic receptors, the number of which may be pathologically-raised in AD/SDAT.

Patent applications have been published which claim the usefulness of a number of steroid sapogenins having spirostance, furo-spirostane, spirosolane or solanidine structures in the treatment of diseases including SDAT. Two patent publications are of particular relevance here: Chinese patent publication No CN1096031A claims the use of the spirostance sapogenin, sarsasapogenin, in the treatment of SDAT. The disclosure in this document, however, is brief. The other document of relevance is patent publication DE 4303214A1 which claims the use of a very wide range of saponins and sapogenins in the treatment of a whole range of diseases that the inventors consider to be of viral origin. This disclosure is however of dubious value in that it is well recognised that there is no infective element to a very large number of the conditions that are characterised by deficient synaptic transmission and thus the basic premise of the alleged invention is flawed. In addition they present no data of any kind that allows one skilled in the art to be able select a preferred compound from the large number that are claimed.

The inventors have found that smilagenin (SMI) exhibits the ability to regulate receptors. In particular, this compound has been found to increase the number of M2 receptors in the brain. Thus, according to one aspect of the invention, there is provided the use of smilagenin in the manufacture of a medication for the treatment of a condition characterised by a deficiency in postsynaptic membrane-bound receptor number or function.

Those skilled in the art will be aware of the relationship between saponins and their sapogenins, and that the latter tend to be fat-soluble whereas the saponins tend to be water-soluble. Sapogenins are therefore better able to cross the blood-brain barrier. The skilled man will also be aware of the epimerisation of certain sapogenins under conditions of acid hydrolysis.

The sapogenin of interest in this invention has the following formula:

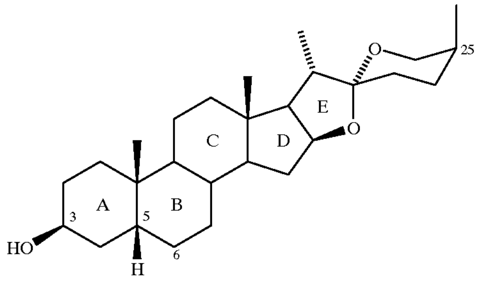

With reference to this general formula, smilagenin has the A/B ring conformation as cis and the stereochemical configuration at the C25 methyl group is R. The hydroxyl group on the spirostane ring is in the 3β-OH position.

Smilagenin occurs naturally in a range of plant species, notably from the genera Smilax, Asparagus, Anemarrhena, Yucca and Agave. The species presently of greatest interest include *Smilax regeli Kilip & Morton*—commonly known as *Honduran sarsaparilla; Smilax aristolochiaefolia Miller*—commonly known as *Mexican sarsaparilla; Smilax ornata Hooker*—commonly known as *Jamaican sarsaparilla; Smilax aspera*—commonly known as *Spanish sarsaparilla; Smilax glabra Roxburgh; Smilax febrifuga—Kunth*—commonly known as Ecuadorian or *Peruvian sarsaparilla; Anemarrhena asphodeloides Bunge; Yucca schidigera Roezl* ex Ortgies; and *Yucca brevifolia Engelm.*

According to a further aspect of the present invention, there is provided a pharmaceutical composition having cognitive function enhancing properties which comprises an effective amount of smilagenin.

In another aspect, the invention provides a pharmaceutical composition having cognitive function enhancing properties which comprises an effective amount of smilagenin in the form of an extract derived from a plant of the genus Smilax, Asparagus, Anemarrhena, Yucca or Agave.

It will be appreciated that the invention embraces within its scope the use of the compositions defined above. Thus, according to a fifth aspect, the present invention provides a method of enhancing cognitive function which comprises administering to a human or animal an effective dosage of a composition of the invention.

The invention also provides a method of enhancing cognitive function in a human or non-human animal, which comprises administering an effective dose of smilagenin.

As used herein, the term "cognitive function" refers to functions such as thinking, reasoning, remembering, imagining and learning.

In identifying compounds that would have use in the treatment of SDAT and other diseases characterised by reductions in receptor numbers or synaptic transmission, the inventors have given consideration to the need to identify compounds that would have the desired effect but would be devoid of any oestrogenic effects, as these would be unacceptable, particularly in male patients. A number of the compounds claimed to have activity in patent application DE 4303214A1 have marked oestrogenic activity and are therefore unacceptable. Smilagenin, however, does not display oestrogenic activity. In addition this compound was tested at other steroid receptors and was found to have no activity at any of the following receptors:

Progesterone

Glucocorticoid

Testosterone

Smilagenin has also been tested for activity in a number of in-vitro assays. The assays/experiments that were considered of key importance in determining possible activity in the elevation of membrane bound receptor numbers were as follows:

1. Chinese hamster ovary (CHO) cells transfected with the a DNA fragment coding for a muscarinic receptor. The cell line used for the majority of the experiments was a cell line expressing the m2 receptor.
2. The effects of muscarinic receptor expression in cultured cell lines of neuronal origin were investigated.
3. Cultured cardiac muscle cells obtained from neonatal Sprague Dawley rats. The cardiac muscle cells express muscarinic receptors, typically m2. The level of these receptors falls on prolonged culture and the effects of compounds of interest in preventing the fall in receptor numbers was investigated.

The methods and the results of these experiments are now described in turn.

1 CHO Cell Line Experiments

The effects of various compounds on the expression of m2 receptors on CHO cells transfected with DNA for the m2 receptor were investigated. Receptor numbers were assayed using tritiated QNB binding and subtracting non-specific binding. Compounds were dissolved in DMSO and DMSO was used as a control. Compounds were tested at a range of final concentrations. Compounds were also tested in the presence and absence of tamoxifen to try to distinguish an oestrogen receptor mediated mechanism. The results are summarised in the Table 1 below, where the compound used in the invention appears in bold, and data on other sapogenins is given for comparative purposes:

TABLE 1

Effects of smilagenin on the expression of $m_2$ receptors on CHO cells

| Compound | Molar concentration of compound | Effect on receptor expression - given as % increase compared to control (negative values in brackets) |
|---|---|---|
| Sarsasapogenin | $10^{-5}$ | 34 |
| | $10^{-6}$ | (14) |
| Anzurogenin D | $10^{-5}$ | 22 |
| | $10^{-6}$ | (26) |
| Sisalgenin | $10^{-5}$ | NS |
| | $10^{-6}$ | NS |
| Smilagenin | $10^{-5}$ | 57 |
| | $10^{-6}$ | 18 |
| Diosgenin | $10^{-5}$ | NS |
| | $10^{-6}$ | NS |
| Ruscogenin | $10^{-5}$ | (22) |
| | $10^{-6}$ | NS |
| Tigogenin | $10^{-5}$ | NS |
| | $10^{-6}$ | NS |

NS = No significant effect

Thus the experiments indicate that smilagenin was able to increase the number of muscarinic receptors expressed on the surface of CHO cells cultured in-vitro. The effect was not antagonised by tamoxifen, indicating that the mechanism involved did not involve the oestrogen receptor.

2 Effects of Smilagenin on Cell Survival

Other in vitro assays have been employed to establish the effects of smilagenin. In particular various neuronblastoma cell lines including SKN-SN and SH-SY5Y cells as well as phaechromoacytoma cell lines have been cultured in vitro in the presence of β-amyloid fragments or serum depletion. A number of techniques to demonstrate the effectiveness of the compounds in protecting the cultured cells were investigated. These techniques included Trypan blue exclusion, chemiluminescence and release of lactate dehydrogenase. Of most interest was the observation that incubation of cells, in particular PC12 cells, with β-amyloid reduced the number of muscarinic receptors measured using radio-labelled ligand binding techniques. This reduction in receptor numbers was found to be ameliorated by smilagenin.

3 Effects of Smilagenin on Cultured Cardiac Muscle Cells

Cardiac muscle cells were isolated from the ventricular muscle of neonatal Sprague Dawley rats using standard techniques. Cells were cultured in vitro and muscarinic receptor numbers expressed on cell surfaces membrane fragments after homogenisation of cells harvested at various time points were estimated using specific binding of tritiated QNB. Preliminary experiments demonstrated that the number of receptors expressed tended to decline after 10 days of culture. The experiments were therefore designed to investigate the effects of the various compounds in inhibiting this decline in receptor numbers.

The results of these experiments are summarised in Table 2, where the compound used in the invention appears in bold, and data on other sapogenins is given for comparative purposes:

TABLE 2

Effects of various compounds on muscarinic receptor expression on cultured cardiac muscle cells

| Compound | Concentration of compound causing a significant increase in number of receptors expressed on neonatal cardiac muscle after 10 days in vitro culture |
|---|---|
| Diosgenin | NS |
| Anzurogenin D | $10^{-6}$M |
| Ruscogenin | NS |
| Sarsasapogenin | $10^{-5}$M |
| Tigogenin | NS |
| Astragaloside | $10^{-5}$M |
| Smilagenin | $10^{-6}$M |

NS = No significant effect

It is speculated here that the effect of the active compound claimed in this patent may operate through an effect on G protein and that the effects on receptor numbers are secondary to an effect on G-protein. When a membrane bound G-protein linked receptor is stimulated two basic sets of events are initiated: the effecter response; and the internalisation of the receptor. The subsequent processing of the receptor to the state where it is again in a form on the cell surface or other membrane surface when it can interact with another receptor ligand appears to be subject to a number of factors. A number of these factors or mechanisms appear to be G-protein linked. There is evidence that activation of $m_3$ receptors may have an effect on G-protein expression or levels. It is speculated that the actions of the compounds described in this patent may due to an interaction in the processes of receptor regeneration, G-protein linkage or G-protein homeostasis.

An alternative hypothesis is that the compounds are increasing the synthesis or release or a decreased rate of degradation of neurotropic factors such as brain derived growth factor and/or nerve growth factor. These effects on growth factors might be due to an effect of the compound on a cytosolic or nuclear receptor or the binding of a compound to a promoter region with a consequent effect directly on the rate of production of mRNA for the growth factor or as a consequence of increasing the production of another material factor such as G-protein or finally the effects may be secondary to an effect on receptor or G-protein procession.

The increased expression and/or abnormal processing of the amyloid precursor protein (APP) is associated with the formation of amyloid plaques and cerebrovascular amyloid deposits which are the major morphological hallmarks of Alzheimer's disease. Of particular interest are the processes regulating the proteolytic cleavage of APP into amyloidogenic and nonamyloidogenic fragments. The cleavage of APP by the enzyme α-secretase within the β-amyloid sequence of the protein results in the formation of a non amyloidogenic C-Terminal fragment, and the soluble APPsα fragment; this latter fragment has been shown to have neurotropic and neuroprotective activity as well as to enhance memory in mice when injected intro-cerebro-ventrically (ICV). In contrast, processing of APP by β-secretase exposes the N-terminus of β-amyloid which is released by γ-secretase cleavage at the variable C-terminus. The resulting β-amyloid peptides, which contain 39–43 amino acids, have been shown to be neurotoxic and to accumulate in plaques which interfere with inter-neurone connections.

A number of studies have shown that stimulation of the protein-kinase (PKC) linked muscarinic $M_1$ and $M_3$ receptors results in an increase in α-secretase activity. As a consequence processing of APP to APPsα with its neuroprotective effects is increased. In parallel, processing of APP by β- and γ-secretase is decreased and there is a consequential reduction of β-amyloid. Other transmitters such as nerve growth factor (NGF) and brain derived neurotropic factor (BDNF) as well as bradykinin and vasopressin may have similar effects in increasing the proportion of APP processed to APPsα. There may be a number of factors involved in the effects of NGF which may include binding of the factor to the tyrosine kinase receptor (TrkA) and the stimulation of phospholipase Cγ with subsequent phosphorylation and activation of protein kinase C (PKC) and increase in relative activity of α-secretase.

Any treatment which increases activity of protein-kinase C selectivity in brain might therefore be expected to be of use in the management of Alzheimer's disease. Until recently agonists selective at the $M_1$ receptor have not been available. Non-selective agonists would be expected to stimulate pre-synaptic $M_2$ receptors which cause negative feedback and hence would further severely impair muscarinic transmission. Selective agonists at the $M_1$ receptor are now becoming available (talsaclidine) and such agents are under investigation for the treatment of AD. There is however, a substantial risk that, as with the chronic administration of any receptor agonist, the clinical benefits seen will be severely limited in terms of the size of benefit by reducing receptor numbers or reducing sensitivity and in terms of side effects due to lack of receptor specificity. Thus compounds as described in this invention, which selectively increase muscarinic $M_1$ receptor numbers, with little or no effect on muscarinic $M_2$ receptor numbers in the brain would be expected to be devoid of the problems seen with a muscarinic agonist and hence have particular utility. Indeed the benefits may be seen in three parts as follows.

1. A selective increase in $M_1$ receptor numbers leading to increased synaptic transmission. Chronic administration of a selective agonist will, at best, have no adverse effect on transmission;
2. Secondary to the increased receptor numbers, an increase stimulation of PKC with a consequential increase in α-secretase activity, leading to:

2.1 A reduced production of β-amyloid and a consequent reduction of plaque formation and neuronal loss;

2.2 An increase in APPsα and a consequent improvement in cerebral function as witnessed by an improvement in short and long term memory.

In order to illustrate the invention further by way of non-limiting example, reference will now be made to the accompanying drawings and to the Examples which follow, in the drawings.

Figure 1:
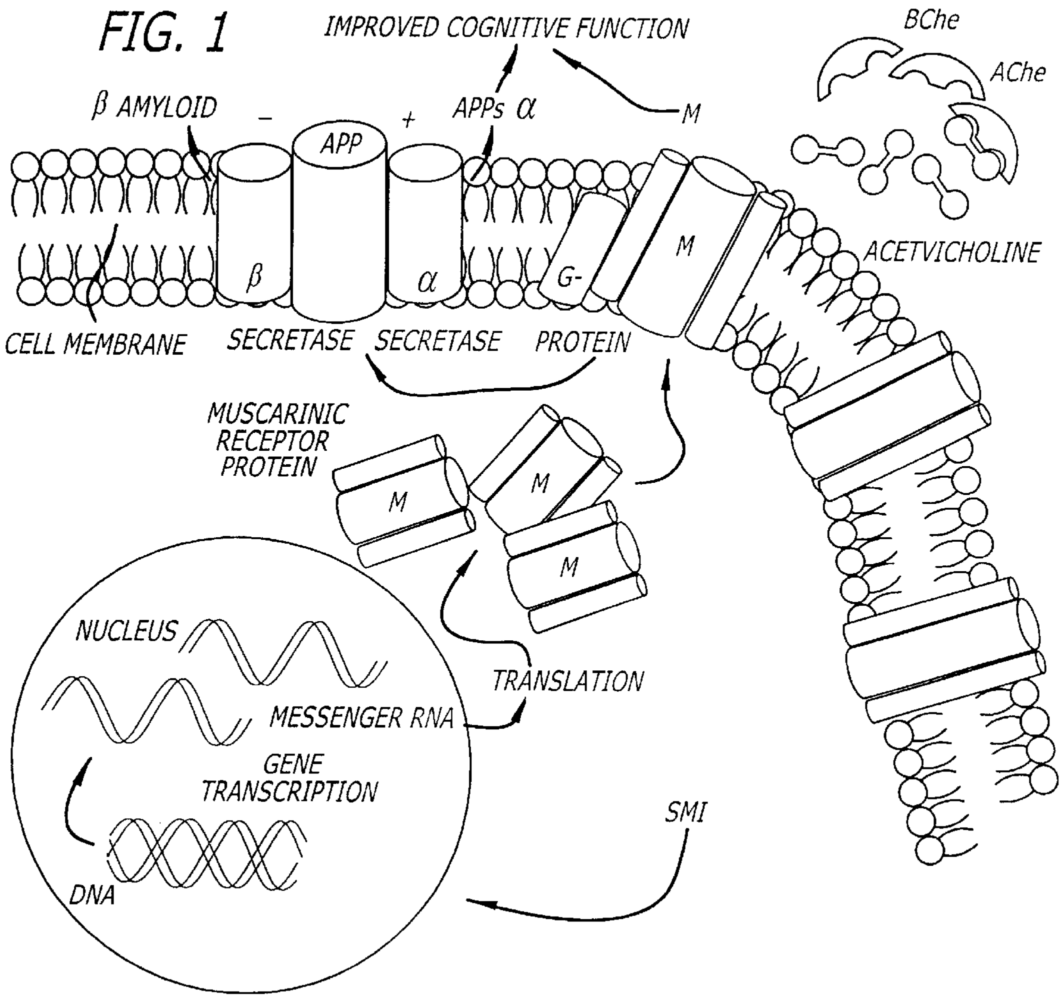
FIG. 1 illustrates a hypothetical mode of action for smilagenin.

Referring to FIG. 1, a diagrammatic representation of the function of smilagenin is shown. It is believed that smilagenin acts primarily on cell nuclei; the invention is not, however, limited to any particular mode of action. The observed increase in muscarinic receptor number consequential upon administration of smilagenin is interpreted as leading to increased expression of muscarinic receptor protein. The possible link between the secretases and β-amyloid protein formation (discussed above) is indicated in the drawing.

The following Examples are provided to illustrate the invention in a non-limiting manner.

EXAMPLE 1

In a CHO cell line expressing recombinant human muscarinic receptors in vitro, the number of muscarinic receptors tends to decline with time. Smilagenin (1–10 $\mu$M), incubated for 72 hours increases muscarinic receptor density.

Methods

Effect of smilagenin on muscarinic receptor density in CHO cells expressing recombinant human muscarinic receptors.

Chinese hamster ovary (CHO) cells expressing high levels of receptor (~2.2 pmoles receptor/mg protein) were cultured in flasks (150 ml) for 24 hours before the start of the experiment. Vehicle (DMSO) and smilagenin (at 1 and 10 $\mu$M) were added to the medium for 48 h. The culture medium was discarded, the cells scraped off and resuspended in Hanks solution, centrifuged and m-receptor levels determined by incubating with [$^3$H]-QNB for 30 min followed by liquid scintillation counting. Protein levels were determined by a micro Lowry method.

Results

Figure 2:
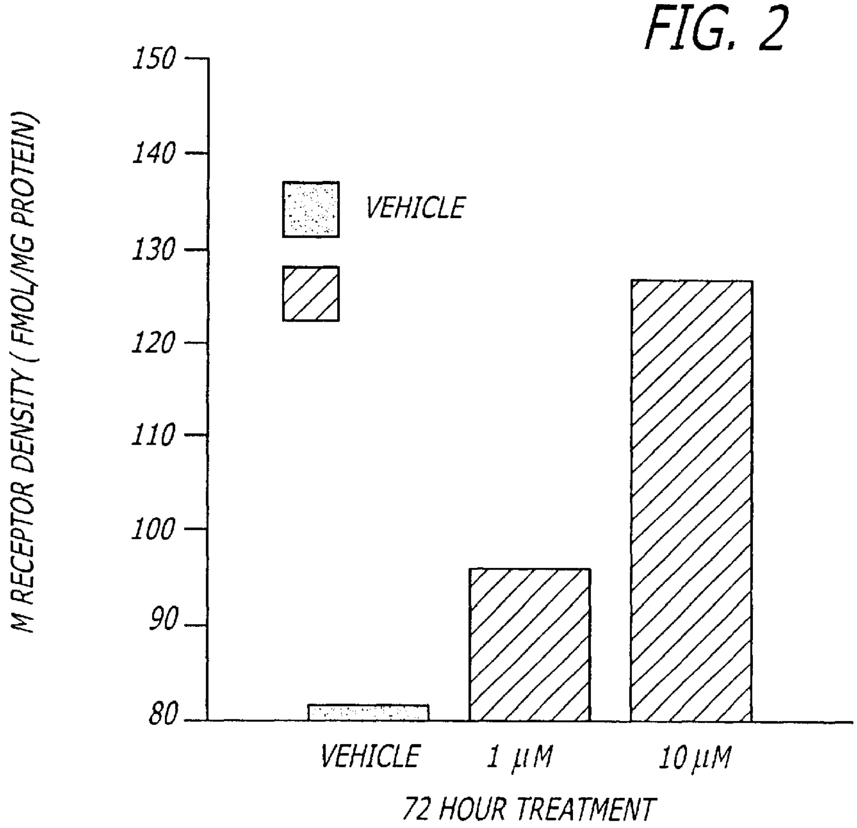
FIG. 2 illustrates the results obtained in Example 1 below.

These are illustrated in FIG. 2. Over the culturing period treatment with smilagenin prevents the decreases in muscarinic receptor number in a concentration-dependent manner.

EXAMPLE 2

Smilagenin (18 mg/kg/day) administered in the food over 3 months reversed the decline in muscarinic (M) receptor number in the brain over this period, restoring levels to close to those observed in young control animals.

Methods: Single point analysis of brain M receptor density

Sprague-Dawley rats, 23-month-old, (i.e. aged) were divided into 2 groups, aged-control and aged+smilagenin. Smilagenin (18 mg/kg/day) was mixed in the chow over the 3 months period. Male 4–6 month old rats acted as young controls. At the end of the 3-month treatment period, pairs of treated and control animals were sacrificed by cervical dislocation and the intact brain removed. Single point analysis of brain M receptor density was obtained.

Results

Figure 3:
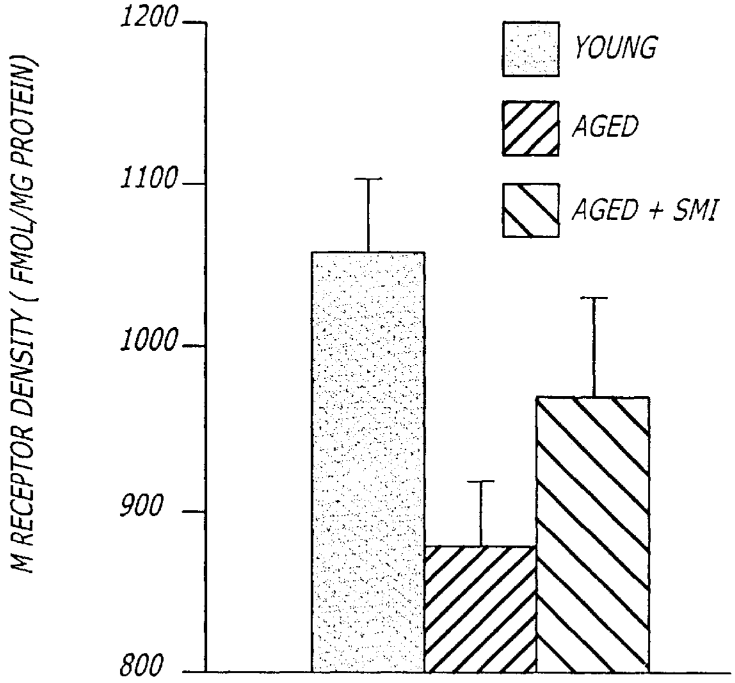
FIG. 3 illustrates the results obtained in Example 2 below.
Figure 1:
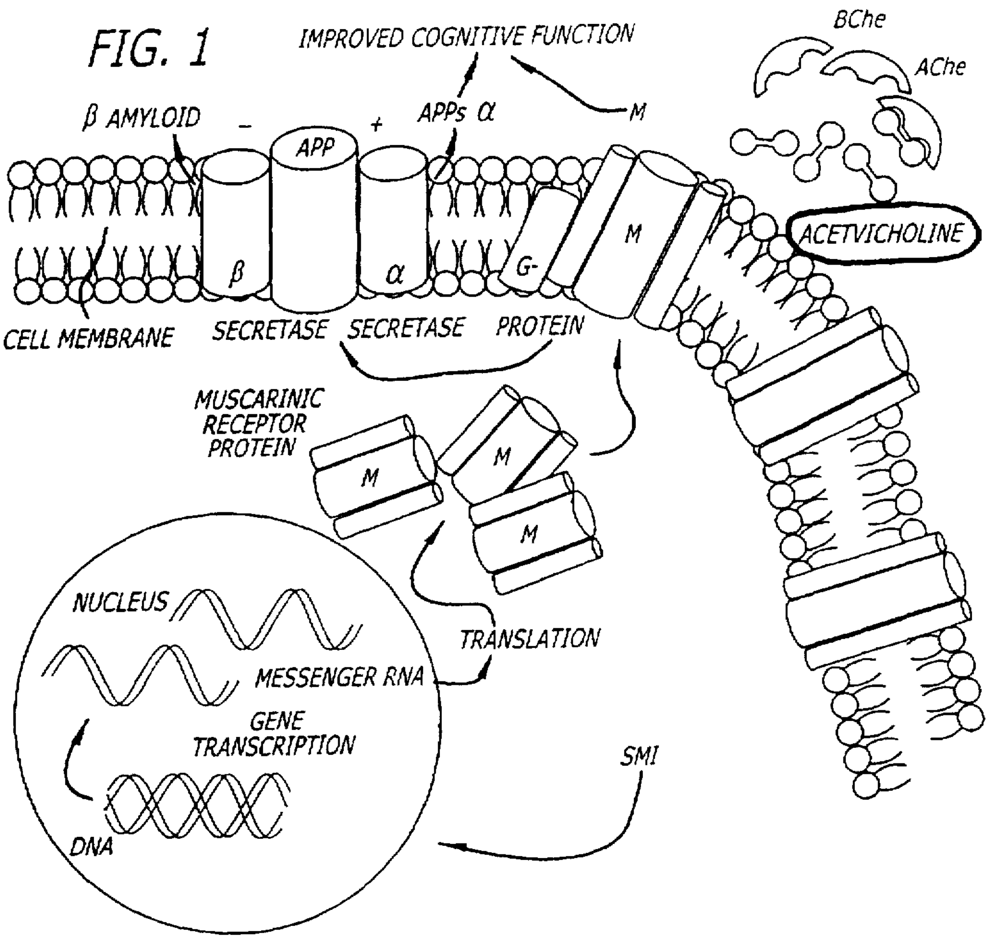
Figure 4:
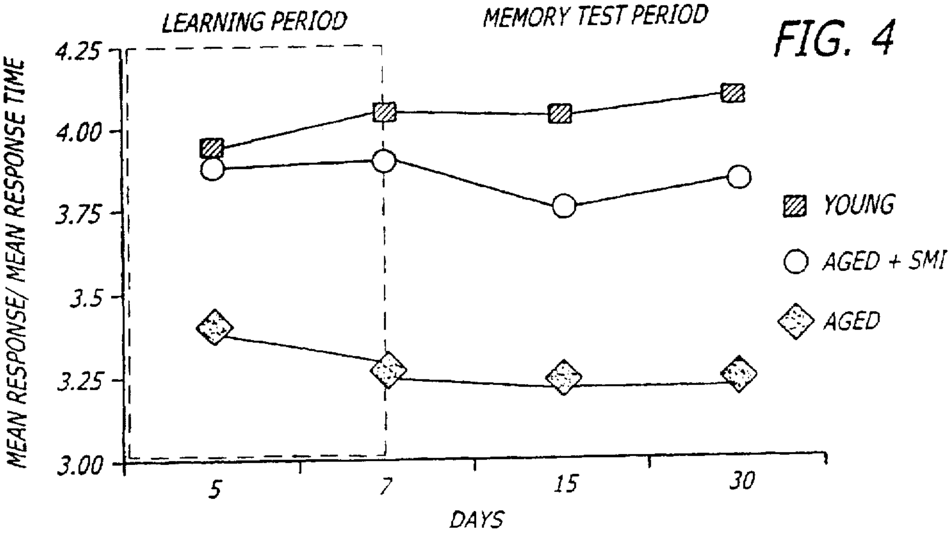
Figure 1:
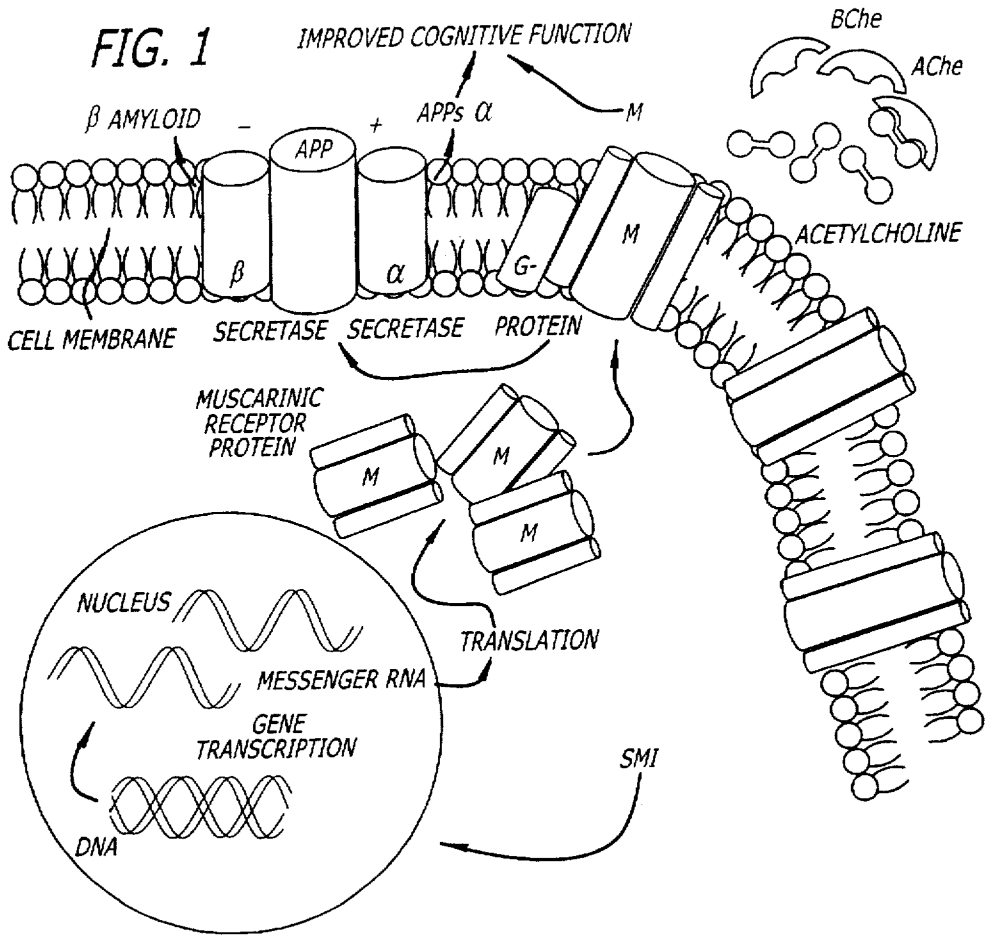
Figure 4:
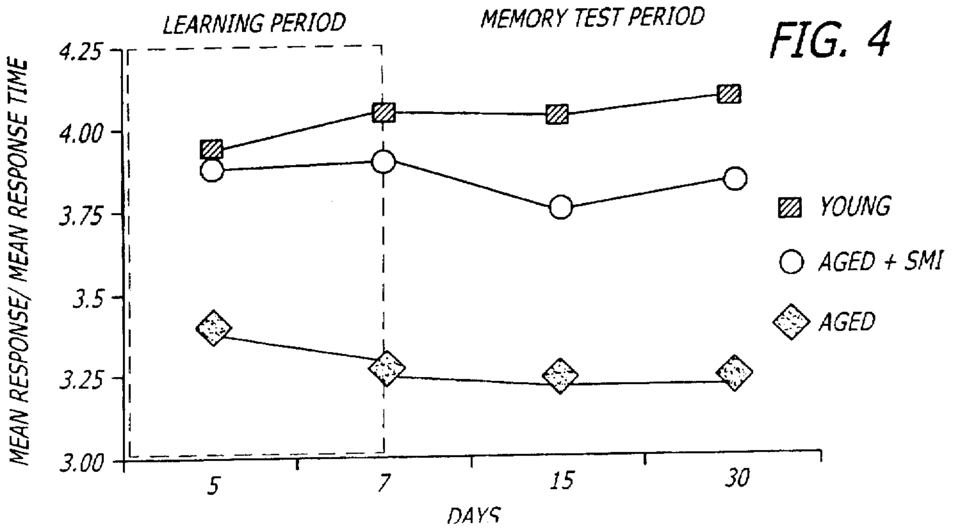

Compared to the young controls there were reductions in M receptor density in brain of the aged controls (FIG. 3). Compared to aged controls, smilagenin increased M receptor numbers. Groups treated with smilagenin were significantly different from untreated controls (FIG. 3).

EXAMPLE 3

Figure 4:
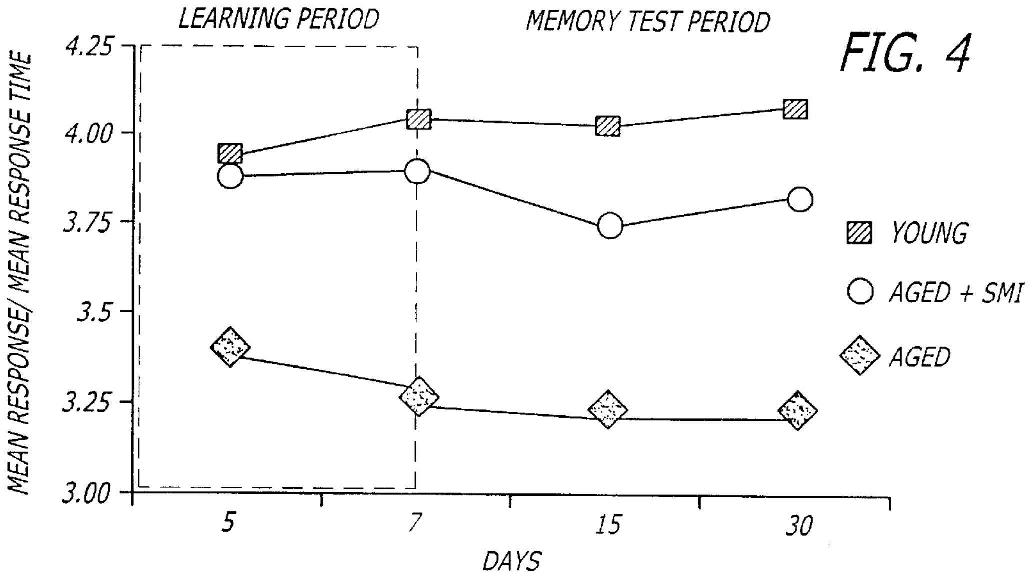
FIG. 4 illustrates the results obtained in Example 3 below. Smilagenin is represented in the drawings by the abbreviation SMI.

Smilagenin (18 mg/kg/day) administered in the food over 4 months reversed the decline in cognitive function over this period compared to that observed in young control animals (FIG. 4).

Methods: Cognitive function in the Y-maze test

Sprague-Dawley rats aged 23 months (i.e. aged) were divided into aged-control or aged+smilagenin treatment group. Rats aged 3 to 4 months acted as young controls. The treatment group received 18 mg/kg/day of smilagenin in chow. Chow without smilagenin was given to each rat after the chow containing smilagenin had been consumed. Three months later the animals were tested in the Y-maze as follows, an equilateral Y-shaped maze was used composed of three 45 cm arms with copper rods in the floor at the end of each arm which conduct electricity and which were 0.2 cm in diameter, 14 cm in length and with a 1 cm gap between them. There were 15 W signal lights at each end. A safe region was indicated by a light signal in an arm where there was no electricity. If a rat moved to a safe region, a correct reaction was recorded. If it moved to an arm where there was no light, an error reaction was recorded. Following the response, an electric shock was again given after a 5 seconds interval. Twenty trials in total were conducted and the correct reaction rate was obtained: number of correct reactions/(20)/mean response time. Seven such training sessions were completed over seven days. Memory tests were then repeated 15 and 30 days later (=4 months) using the same techniques as just described.

Results

Compared to young control rats, aged control animals have a reduced learning and memory performance in the Y-maze tests. A regime of 3 months intake of smilagenin (18 mg/kg/day) reversed the decline in cognitive function (FIG. 4), giving results comparable to those of young animals.

What is claimed is:

1. A method enhancing cognitive function in a human or non-human animal, which comprises administering an effective dose of smilagenin.

2. A method of enhancing cognitive function in a patient suffering from age-related cognitive dysfunction, which comprises administering to the patient a pharmacologically effective dose of smilagenin.

3. A method as claimed in claim 1, which is for the treatment of Alzheimer's disease or a senile dementia of the Alzheimer's type.

4. A method as claimed in claim 2, which is for the treatment of Alzheimer's disease or a senile dementia of the Alzheimer's type.

5. A method according to claim 1 which comprises administering a foodstuff or beverage containing an effective dosage of smilagenin.

6. A method as claimed in claim 1 wherein smilagenin is administered in the form of a pharmaceutical composition.

7. A method as defined in claim 1 wherein smilagenin is administered in the form of a pharmacologically effective amount of smilagenin in the form of an extract derived from a plant of the genus Smilax, Asparagus, Anemarrhena, Yucca or Agave.

8. A method as defined in claim 1 wherein a dosage effective to enhance cognitive function is administered to a person suffering from loss of cognitive function.

* * * * *

UNITED STATES PATENT AND TRADEMARK OFFICE
CERTIFICATE OF CORRECTION

PATENT NO. : 6,258,386 B1
DATED : July 10, 2001
INVENTOR(S) : Zongqin Xia et al.

It is certified that error appears in the above-identified patent and that said Letters Patent is hereby corrected as shown below:

Drawings,
A typographical error is in FIG. 1 (at right hand corner of figure) where the neotransmitter ACETYLCHOLINE is wrongly named as ACETVICHOLINE.

A copy of the incorrect drawing (error circled in red) and a corrected drawing are enclosed.

Signed and Sealed this

Nineteenth Day of March, 2002

*Attest:*

JAMES E. ROGAN

*Attesting Officer*

*Director of the United States Patent and Trademark Office*

UNITED STATES PATENT AND TRADEMARK OFFICE

CERTIFICATE OF CORRECTION

PATENT NO. : 6,258,386 B1
DATED : July 10, 2001
INVENTOR(S) : Zongqin Xia et al.

It is certified that error appears in the above-identified patent and that said Letters Patent is hereby corrected as shown below:

Column 10,
Lines 30-32, claim 1 should read:

1. A method of enhancing cognitive function in a human or non-human animal, which comprises administering an effective dose of smilagenin.

Signed and Sealed this

Fourteenth Day of January, 2003

JAMES E. ROGAN
*Director of the United States Patent and Trademark Office*